United States Patent
Fomitchev

(10) Patent No.: US 6,167,758 B1
(45) Date of Patent: Jan. 2, 2001

(54) METHOD AND APPARATUS FOR GENERATING ULTRASONIC PULSES WITH A SPECIFIED WAVEFORM SHAPE

(76) Inventor: Max I. Fomitchev, 3814 S. Cincinnati Ave., Tulsa, OK (US) 74105

( * ) Notice: Under 35 U.S.C. 154(b), the term of this patent shall be extended for 0 days.

(21) Appl. No.: 09/177,346

(22) Filed: Oct. 23, 1998

(51) Int. Cl.[7] .................................................. G01N 29/04
(52) U.S. Cl. .............................................................. 73/602
(58) Field of Search ............................ 73/602, 632, 642, 73/626, 625, 628

(56) References Cited

U.S. PATENT DOCUMENTS

| | | | |
|---|---|---|---|
| 4,080,660 | * 3/1978 | Constant | 364/715 |
| 4,164,740 | * 8/1979 | Constant | 343/5 CM |
| 4,222,274 | 9/1980 | Johnson . | |
| 4,228,517 | * 10/1980 | Constant | 364/724 |
| 4,243,935 | * 1/1981 | McCool et al. | 324/77 R |
| 4,387,597 | * 6/1983 | Brandestini | 73/626 |
| 4,520,670 | 6/1985 | Salomousson . | |
| 5,675,554 | 10/1997 | Cole . | |

* cited by examiner

Primary Examiner—Hezron Williams
Assistant Examiner—Rose M. Miller

(57) ABSTRACT

A method and an apparatus for generating ultrasonic pulses of a specified waveform shape w(t) using an ultrasonic transducer (2) includes a power amplifier (6), a memory (9) for storing a signal for excitation of the ultrasonic transducer (2) and a control logic (4). The stored excitation signal is supplied to the transducer (2) via a digital-to-analog converter (5). Repeated adjustment of the stored excitation signal can be effected by supplying, via an analog-to-digital converter (8), the echo pulse signals from the ultrasonic transducer (2) or the output voltage of the power amplifier (6) to the control logic (4) for analysis. The stored excitation signal is substantially an optimal lag filter $f_L(t)$ proper to the transducer and the desired output waveform w(t). The optimal lag filter $f_L(t)$ is calculated as follows: for all reasonable values of lag l a lag filter $f_l(t)$ is calculated for the delayed desired output waveform w(t)→w(t−1); lag filter quality $P(f_l(t))$ is evaluated; and the optimal lag filter $f_L(t)$ is selected corresponding to the value of lag L yielding the best filter quality.

13 Claims, 6 Drawing Sheets

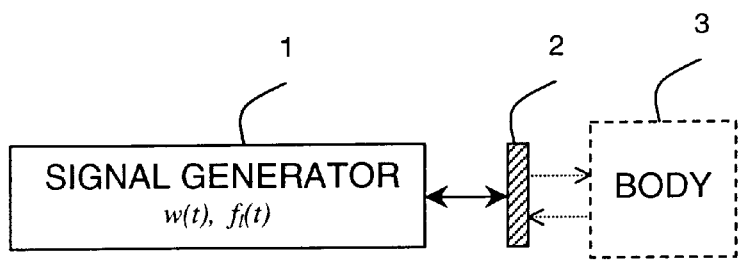
FIG. 1
FIG. 2
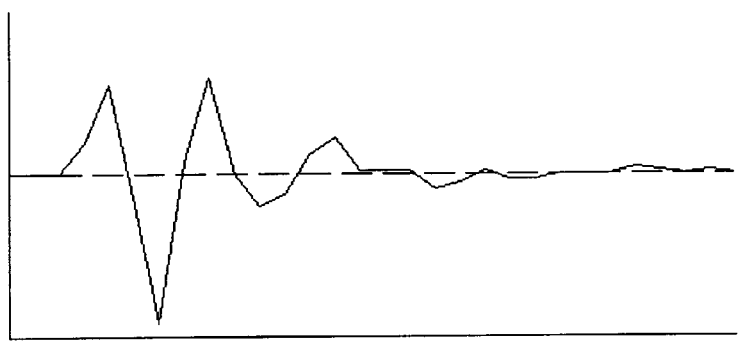
FIG. 3a
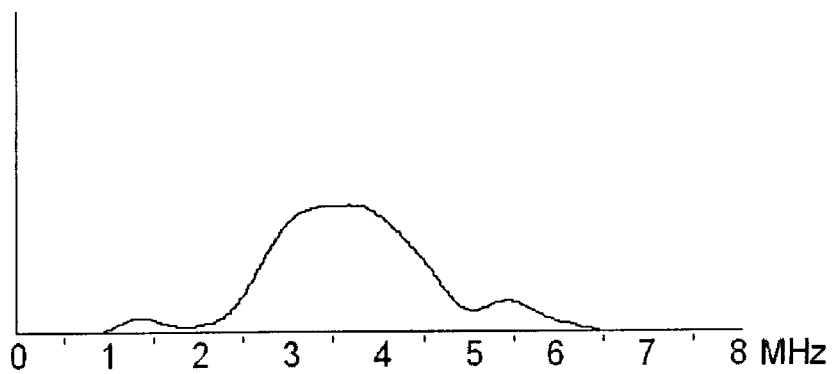

METHOD AND APPARATUS FOR GENERATING ULTRASONIC PULSES WITH A SPECIFIED WAVEFORM SHAPE

BACKGROUND

1. Field of Invention

This invention relates to a method and an apparatus for generating ultrasonic pulses with a precisely specified waveform shape.

2. Description of Prior Art

Ultrasound imaging devices are widely used in medicine and industry for non-destructive/non-invasive study of interior of objects.

These devices produce a beam of ultrasonic energy, which travels through the object under investigation. An echosignal is formed by reflections resulting from inhomohenities or interfaces within the object.

Lateral resolution of a pulsed-echo ultrasound imaging system depends on the ultrasonic beam width. Axial resolution depends on the ultrasonic pulse duration.

The lateral resolution is improved by means of static or dynamic focusing using acoustic lenses or electronically focused transducer arrays. The width of the focused ultrasonic beam is proportional to its wavelength.

The axial resolution is improved by using high frequency ultrasound or making the ultrasonic pulses shorter. However the high frequency ultrasound limits depth of penetration due to attenuation, increasing as some power of the pulse frequency.

Normally a transducer is excited by a sharp voltage spike. In this case the length of the transducer impulse response function limits the duration of the ultrasonic pulse. Mechanical damping of the transducer allows reducing the impulse response function length by the cost of sacrificing the transducer sensitivity. This is often unacceptable since in most cases the same transducer is used for transmission and reception of ultrasonic signals.

Thus in order to overcome this problem different excitation voltage waveform must be applied to the transducer. The shape of the excitation voltage waveform ultimately determines the shape and duration of the transmitted ultrasonic pulse.

Attempts to control the transmitted ultrasonic pulse waveform can be traced in the following patents: in U.S. Pat. No. 4,222,274 to Steven A. Johnson (1978) an apparatus is proposed capable of transmitting ultrasonic beams of two predetermined shapes; in U.S. Pat. No. 4,520,670 to Göran Salomonsson et. al. (1982) a method and an apparatus is proposed for generating short ultrasonic pulses by means of an excitation signal shaped as a weighted least squares filter; a complex beamformer is described in U.S. Pat. No. 5,675,554 to Christopher R. Cole et al. (1996) which is capable of producing focused ultrasonic beams having a specified carrier frequency and envelope.

Nevertheless it is still desirable to be able to produce ultrasonic pulses having a variety of precisely specified waveforms including those which can not be specified in terms of carrier frequency and envelope.

The specified waveform will determine the frequency spectrum and the wavelength of the transmitted ultrasonic pulse thus enabling the use of the same transducer for different applications such as near field and far field examinations. The precise shape of the transmitted ultrasonic pulse can be selected to facilitate image reconstruction techniques such as deconvolution or wavelet transform resulting in the improved lateral and axial resolution and superior image quality.

OBJECTS AND ADVANTAGES

The key advantage of the present invention is the means of precise control over the transmitted ultrasonic pulse waveform and frequency.

Another advantage of this invention is the ability to transmit ultrasonic pulses, which can not be specified in terms of carrier frequency and envelope.

Yet another advantage of this invention is the simplicity of the method and the apparatus implementation.

DRAWING FIGURES

In the drawings, closely related figures have the same number but different alphabetical suffixes.

FIG. 1 illustrates the basic principle of this invention in an apparatus according to the invention.

FIG. 2 illustrates the shaping filter lag concept.

FIGS. 3a and 3b show the impulse response and the power spectrum functions of an ultrasonic transducer.

REFERENCE NUMERALS IN DRAWINGS

Figure 4A:
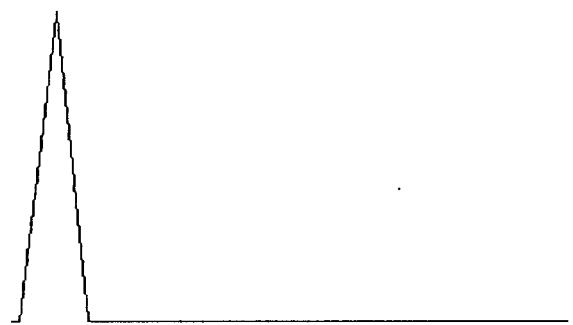
FIGS. 4a, 4b and 4c depict the desired output of the inverse least squares filter, the shape of the optimal lag least squares filter and the actual filter output.
Figure 4B:
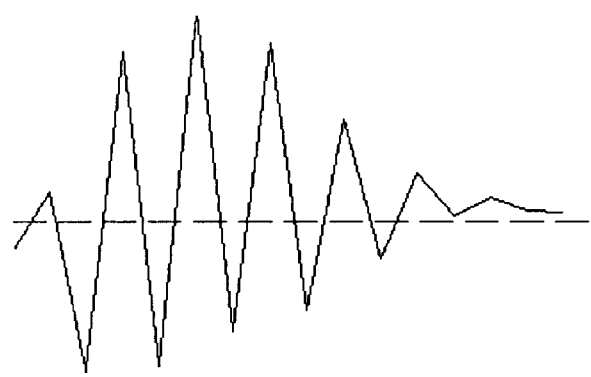
Figure 4C:
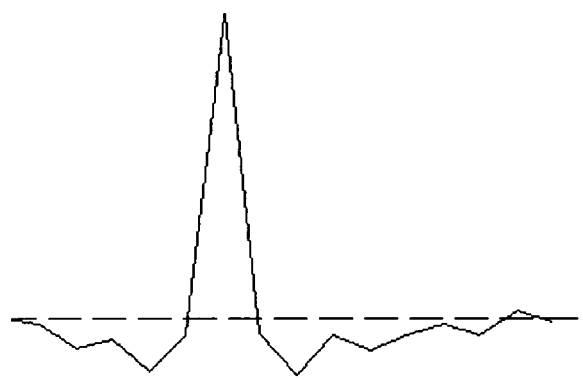

| | |
|---|---|
| 1 | signal generator |
| 2 | ultrasonic transducer |
| 3 | body |
| 4 | control logic |
| 5 | digital-to-analog converter |
| 6 | power amplifier |
| 7 | input amplifier |
| 8 | analog-to-digital converter |
| 9 | memory |

Summary

According to the invention, ultrasonic pulses having the precisely specified waveform are generated by exciting a transducer with a signal which substantially is a shaping lag filter proper to the transducer and the desired waveform shape.

Description—FIGS. 1 to 5

The apparatus according to the invention is shown on FIG. 1 and comprises a signal generator 1 which is coupled to an ultrasonic transducer 2 for the excitation thereof. The ultrasonic pulses are emitted into a body 3 and the echosignal is recorded and analyzed.

According to the present invention the signal generator 1 is adapted to generate an excitation signal which substantially constitutes a shaping lag filter proper to the transducer 2 and the desired output waveform w(t).

The present invention is a method and related apparatus for producing ultrasonic pulses of the desired waveform shape by means of an ultrasonic transducer. Detailed description of the invention follows.

It is know in the art that a piezoelectric ultrasonic transducer can be treated as a linear system with the impulse response function g(t). It means that when the system is excited with the signal w(t) it produces an output signal $$h(t)=w(t)*g(t) \quad (1)$$

where '*' indicates convolution. Thus in order to make the system to produce the output signal in the desired form w(t) we must feed the system an input signal $$f(t)=w(t)*g^{-1}(t) \quad (2)$$

where $g^{-1}(t)$ is the inverse of g(t) and $$g(t)*g^{-1}(t)=\delta(t) \quad (3)$$

where $\delta(t)$ is delta-function.

According to (1) the system with the impulse response g(t) excited by the input signal f(t) produces equivalent to the desired waveform w(t):

$$f(t)*g(t)=w(t)*g^{-1}(t)*g(t)=w(t)*\delta(t)=w(t) \quad (4)$$

The shaping filter function f(t) can be obtained by solving the general deconvolution problem. One way of calculating the shaping filter f(t) employs conventional Fourier technique:

$$f(t)=FT^{-1}(FT(w)/FT(g)) \quad (5)$$

where FT is forward Fourier transform, and $FT^{-1}$ is inverse Fourier transform.

Also f(t) can be calculated using the least squares error criterion by minimizing cost function of the form $$I = \int_{-\infty}^{+\infty} (f(t)*g(t) - w(t))^2 dt \quad (6)$$

Both methods yield substantially the same results and can be applied to discrete, digitally sampled signals.

In discrete domain the impulse response function of the system g(t) is sampled on m evenly spaced points on the time interval of the transducer impulse response duration. The desired waveform w(t) can be specified as a set of n evenly spaced points on the time interval of its duration. For the sake of simplicity we assume that both functions are sampled with the same frequency $f_0$ and contain the same number of points m (we can always pad a shorter function with zeros). Also we assume that w(0)=0, w(1)≠0 and w(m−1)=0, that means that the desired waveform is left-padded by a single zero and ends with a zero.

The finite nature of the functions imposes inherent limitations on the quality of the actual output signal w'(t) which only approximates the desired output w(t).

Having discrete functions g(t) and w(t) the equation (6) can be rewritten as $$I = \sum_{t=0}^{m-1} (f(t)*g(t) - w(t))^2 \quad (7)$$

where the least squares shaping filter f(t) is also discrete and has m coefficients.

The quality P of a least squares shaping filter is defined by the following equation:

$$P = \sum_{t=0}^{m-1} f(t) \frac{\phi_{wg}(t)}{\phi_{ww}(0)} \quad (8)$$

where $\phi_{wg}(t)$ is cross-correlation between the input signal g(t) and the desired output w(t), $\phi_{ww}(0)$ is autocorrelation of the desired output function w(t).

Cross-correlation $\phi_{ab}(\tau)$ is defined as $$\phi_{ab}(\tau) = \sum_{t=0}^{\infty} a(t+\tau) b(t) \quad (9)$$

$0 \leq P \leq 1$, P=0 corresponds to the worst possible filter, while P=1 corresponds to the best possible filter.

The quality of the filter depends on the impulse response g(t) of the system under consideration, the desired output w(t) and the filter length m. In general the more coefficients the filter has the better the filter quality.

Having the system impulse response g(t) and the desired output w(t) we can compute the shaping filter f(t) by minimizing the expression (7). This minimization results in the system of linear equations $$\sum_{t=0}^{m-1} f(t) \phi_{gg}(j-t) = \phi_{wg}(j), \quad j=0, 1, \ldots m-1 \quad (10)$$

which can be solved efficiently using Toeplitz recursion. The actual output of the system will be $$w'(t)=f(t)*g(t) \quad (11)$$

We can improve the quality of the actual output w'(t) by sampling w(t) and g(t) more accurately (i.e. having more sampling points) and by increasing the length of the filter m.

However due to practical limitation we can not set m arbitrarily large.

A novel and unobvious method for improving quality of the output of the system employs repetitive time shifting of the desired output for computation of the shaping filter. In other words the shaping filter lag l is varied. The concept of shaping filter lag is illustrated on FIG. 2.

In attempt to yield better filter quality and keeping in mind that the quality of the actual output w'(t) depends on the shape of the desired output w(t) we can time shift the desired output w(t)→w(t−l) and design a shaping lag filter $f_l(t)$ for the w(t−l), rather than for w(t). The ultimate shape of w(t) is preserved and the lag l represents only the delay of the output signal with respect to the input, which is not critical.

For any given desired output w(t) the shaping filter is calculated for all possible lag values: l=0, 1, . . . m−1. The filter with the best quality is selected and is called the optimal lag filter.

Least squares shaping lag filters are known in the field geophysics and used for seismic data processing. However the concept of shaping lag filter is extended within the scope of this invention to cover all types of convolution filters, including pure inverse, matched and Wiener filters.

To summarize, the process of computing of the optimal lag shaping filter for the desired output w(t) consists of the following steps:

1. Obtain an impulse response function of the system g(t), t=0, 1, ... m−1.

2. For each value of l=0, 1, ... m−1 time-shift the desired output: w(t)→w(t−l)

calculate shaping filter $f_l(t)$ calculate shaping filter quality or error

3. Select the optimal lag filter corresponding to the best quality or minimal error.

The algorithm above can be rewritten in a more specific form for the optimal lag least squares filter calculation:

1. Obtain an impulse response function of the system g(t), t=0, 1, ... m−1.

2. For each value of l=0, 1, ... m−1 time-shift the desired output: w(t)→w(t−l)

calculate shaping filter $f_l(t)$ by solving (10) by means of Toeplitz recursion calculate shaping filter quality $P_l$ 3. Select the optimal lag filter corresponding to the best quality (i.e. largest value of $P_l$).

A transducer impulse response function is shown on FIG. 3a and its power spectrum is shown on FIG. 3b. The impulse response central frequency is 3.5 MHz. A desired output w(t) shaped as a spike is shown on FIG. 4a. The corresponding optimal lag least squares filter shape is shown on FIG. 4b, the filter length m=16, lag l=6. And the actual filter output w(t) is shown on FIG. 4c. As it is seen that w'(t) approximates w(t), the filter quality P=0.83.

When f(t) is stored digitally in memory and then supplied to a transducer via a digital-to-analog converter (DAC) coupled to a power amplifier the quality of the signal will be limited by the linearity of the power amplifier. Since it is not possible to design a perfectly linear system, the actual output w"(t) can be expressed as $$w''(t)=f(t)*(g(t)+e(t))=f(t)*g(t)+f(t)*e(t)=w'(t)+n(t) \quad (12)$$

where e(t) is a random error, modeling imperfection of the system.

Thus in a not perfectly linear system the actual output will be distorted by the presence of noise n(t). In such a system the length of the shaping filter f(t) may play a critical role because long excitation pulses in combination with not perfectly linear power amplifier will result in significant increase of noise due to the error accumulation.

Figure 5:
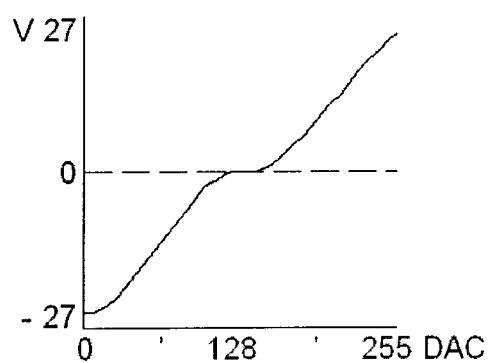
FIG. 5 depicts the dependence between digital-to-analog converter values and a power amplifier output voltage.

Further improvement of the resulting ultrasonic pulse shape can be achieved when taking into account the power amplifier transfer function or DAC values-to-voltage map (FIG. 5). Generally this curve won't be a perfect line and must be properly accounted for in order to decrease the magnitude of the distorting error e(t). The curve can be produced by setting a specific value on the DAC input and measuring the output voltage of the power amplifier connected to a transducer.

When the optimal lag shaping filter values are adjusted according to the curve the quality of the output increases dramatically.

Operation—FIGS. 6 to 9c

Figure 6:
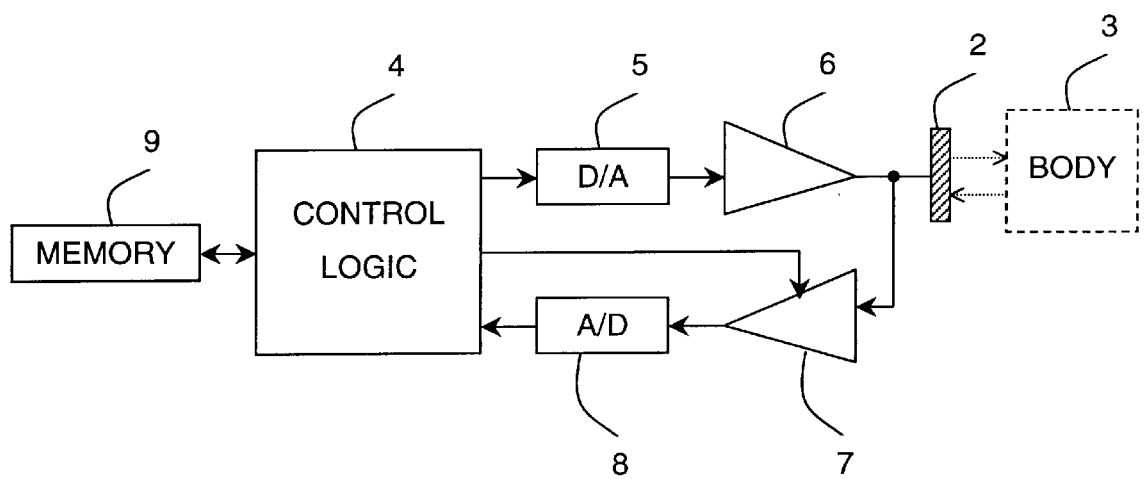
FIG. 6 shows a block diagram of the test equipment incorporating the invention.

The test equipment used for the experiments is illustrated on FIG. 6. The equipment comprises an ultrasonic transducer 2 adjacent to a body 3. The excitation signal which is substantially an optimal lag shaping filter is stored in a memory 9 in digital form and supplied to a digital-to-analog converter (DAC) 5 by means of a control logic 4. The output of DAC 5 is connected to the excitation input of the transducer 2 via a power amplifier 6. The transducer 2 emits its pulses towards the body 3 and receives echosignals therefrom. The echosignals converted into electrical form by the transducer 2 are supplied via an input amplifier 7 and an analog-to-digital converter 8 to the control logic 4 for evaluation and analysis. The control logic 4 is connected to the input amplifier 7 by means of an additional signal path providing means for controlling the input amplifier gain and the input voltage range.

Obviously, it is possible with an apparatus devised in analogy with the test equipment according to FIG. 6, to carry out repeated adjustment of the excitation signal by inserting the resulting echosignal in some suitable algorithm. For example such algorithm could adjust values of the shaping filter coefficients according to the shape of the received echosignal in order to minimize the residual oscillations.

Also, it is possible with an apparatus devised in analogy with the test equipment according to FIG. 6, to carry out repeated adjustment of the excitation signal by sampling the output of the power amplifier and adjusting the excitation waveform accordingly.

Figure 7A:
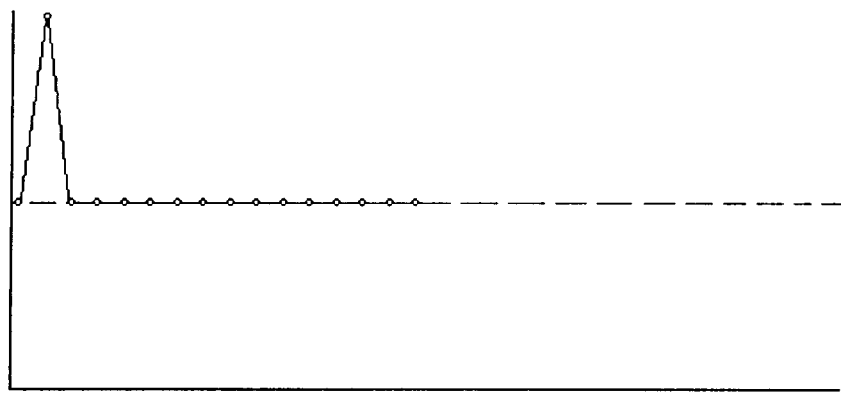
FIGS. 7a, 7b and 7c show the desired pulse waveform shaped as delta-function, the transmitted ultrasonic pulse waveform and its power spectrum.
Figure 7B:
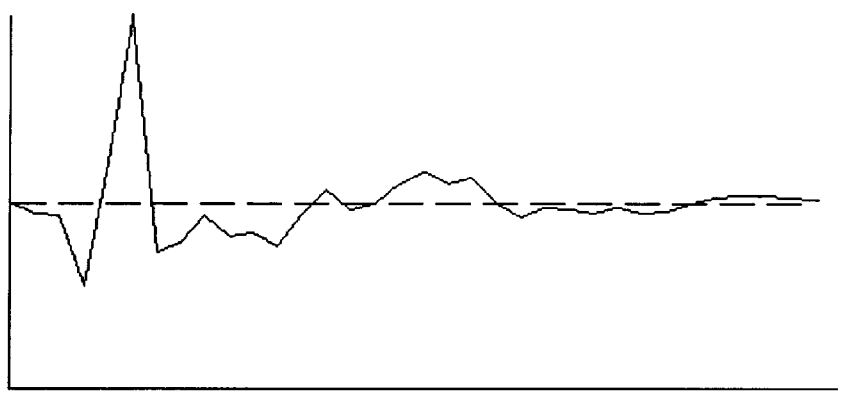
Figure 7C:
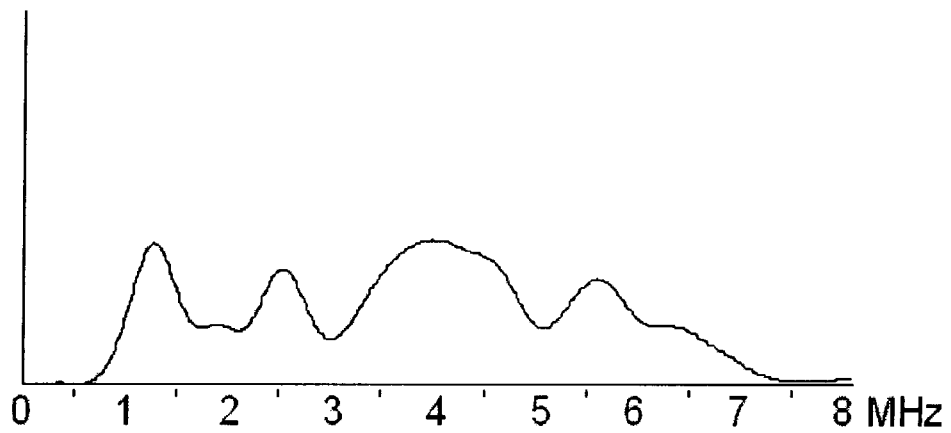

FIG. 7a shows the desired pulse waveform shaped as delta-function (m=16). The actual transmitted ultrasonic waveform and its power spectrum, produced when exciting the transducer with the optimal lag shaping filter corresponding to the desired waveform are shown on FIGS. 7b and 7c respectively. The pulse central frequency shifted from 3.5 to 4 MHz.

Figure 8A:
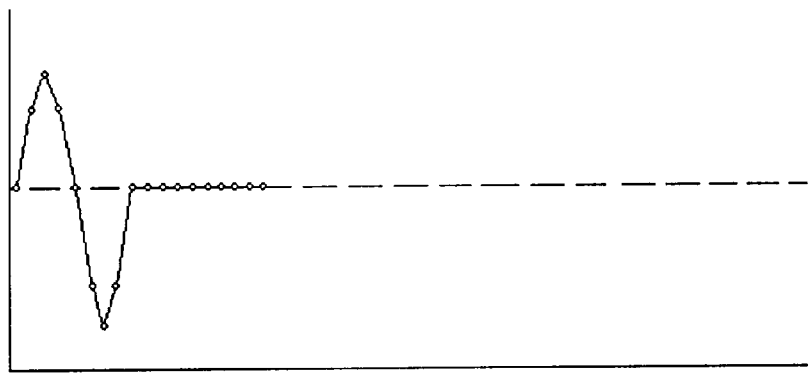
FIGS. 8a, 8b and 8c show the desired pulse waveform shaped as one period of 2-MHz sine wave, the transmitted ultrasonic pulse waveform and its power spectrum.
Figure 8B:
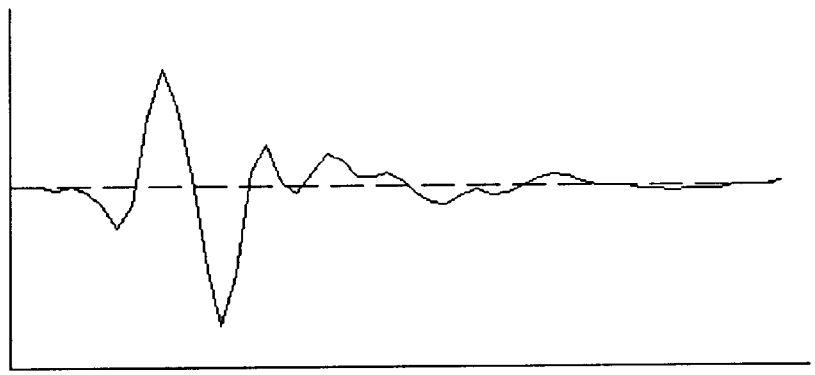
Figure 8C:
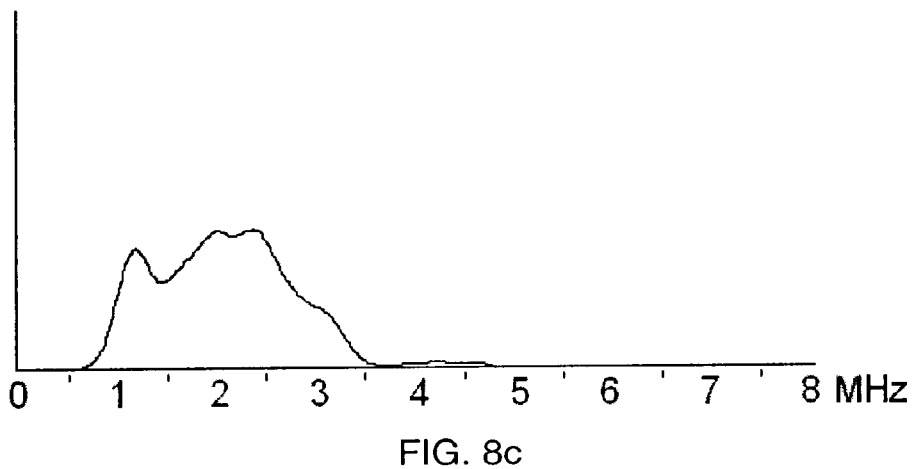
Figure 9A:
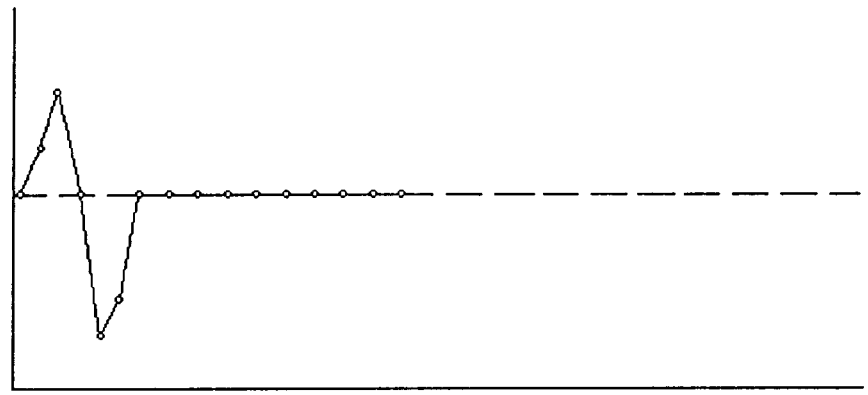
FIGS. 9a, 9b and 9c show the desired pulse waveform shaped as one period of 3.5-MHz resonance oscillations of the transducer, the transmitted ultrasonic pulse waveform and its power spectrum.
Figure 9B:
Figure 9C:
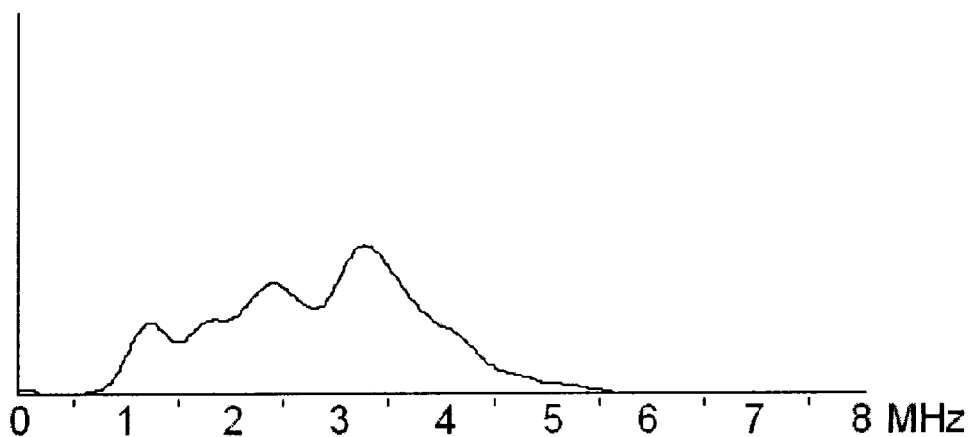

FIG. 8a shows the desired pulse waveform shaped as one period of a 2-MHz sine wave. The actual transmitted ultrasonic waveform and its power spectrum, produced when exciting a transducer with the optimal lag shaping filter corresponding to the desired waveform are shown on FIGS. 8b and 8c respectively. The central frequency of the transmitted pulse is 2 MHz and it matches the frequency of the specified sine wave. The actual transmitted waveform closely matches the desired one. FIGS. 9a, 9b and 9c illustrate electronic damping of the transducer impulse response. The desired pulse waveform shown on FIG. 9a is shaped as the first two resonance oscillations of the transducer impulse response shown on FIG. 3a. The actual transmitted ultrasonic waveform and its power spectrum, produced when exciting a transducer with the optimal lag shaping filter corresponding to the desired waveform are shown on FIGS. 9b and 9c respectively. The transmitted ultrasonic waveform closely matches the first two oscillations of the pulse shown on FIG. 3a. All the residual oscillations are damped.

Conclusion, Ramifications, and Scope

According to the invention, ultrasonic pulses with the precisely specified waveform are generated by imparting to the method and the apparatus the special features of which are stated in the appended claims.

Based on the experimental results it is seen that the proposed technique allows precisely controlling the transmitted ultrasonic pulse waveform and frequency, displaying a clear advantage over the prior art.

In addition the simplicity of the method and the related apparatus makes the invention easy to implement.

Although the description above contains much specificity, these should not be construed as limiting the scope of the invention but as merely providing illustration of the presently preferred embodiment of this invention. For example, other methods than described can be used to calculate the shaping lag filter proper to the transducer and to the desired waveform shape; the desired waveform shape can be specified as power spectrum; other amplification means can be used to amplify the excitation signal supplied to the transducer excitation input; the method can be used to control transducer arrays, sonars, etc.

It will be appreciated that numerous modifications of the embodiments described can be effected within the scope of this invention.

What is claimed is:

1. A method for generating ultrasonic pulses of a specified waveform shape w(t) by means of an ultrasonic transducer, including the steps of:

generating an excitation signal having the shape of a lag filter $f_l(t)$ proper to the transducer and the desired output waveform w(t);

exciting said ultrasonic transducer with said excitation signal.

2. A method as claimed in claim 1, wherein said lag filter is an optimal lag filter $f_L(t)$ calculated for the optimally delayed desired output waveform w(t)→w(t−L) corresponding to the value of lag L yielding the best filter quality.

3. A method as claimed in claim 2, wherein said optimal lag filter is an optimal lag least squares filter.

4. A method as claimed in claim 2, characterized in that electronic dumping of said ultrasonic transducer is effected by specifying said desired output waveform w(t) to match the first few oscillations of the transducer impulse response.

5. A method as claimed in claim 2, characterized in that the transfer function is utilized to adjust said optimal lag filter function.

6. A method as claimed in claim 5, characterized in that said optimal lag filter function is calculated repetitively for repeated adjustments of the excitation signal of the transducer.

7. A method as claimed in claim 5, characterized in that said optimal lag filter function is stored in digital form in memory and supplied to said ultrasonic transducer via a digital-to-analog converter.

8. An apparatus for generating ultrasonic pulses of a specified waveform shape w(t) comprising:

an ultrasonic transducer having an excitation input;

a signal generation means, adapted to generate an excitation signal having the shape of a lag filter $f_l(t)$, having an output connected to the excitation input of said ultrasonic transducer.

9. An apparatus as claimed in claim 8, wherein said lag filter is an optimal lag filter $f_L(t)$ calculated for the optimally delayed desired output waveform w(t)→w(t−L) corresponding to the value of lag L yielding the best filter quality.

10. An apparatus as claimed in claim 8, wherein said signal generation means further comprises:

a memory for said excitation signal;

a signal amplification means having an output connected to the excitation input of said ultrasonic transducer;

a digital-to-analog converter connecting the output of said memory with the input of said signal amplification means.

11. An apparatus as claimed in claim 10, wherein said signal amplification means comprises a plurality of power amplifiers.

12. An apparatus as claimed in claim 11, further comprising:

a control logic means;

an analog-to-digital converter having an input connected to said ultrasonic transducer for receiving electrical signals corresponding to ultrasonic echo pulses, and the output connected to said control logic means, the output of the analog-to-digital converter being a digital signal used for repeated adjustment of the excitation signal.

13. An apparatus as claimed in claim 11, further comprising:

a control logic means;

an analog-to-digital converter having an input connected to said ultrasonic transducer for receiving electrical signals corresponding to the amplified excitation signals, and the output connected to said control logic means, the output of the analog-to-digital converter being a digital signal used for repeated adjustment of the excitation signal.

* * * * *